United States Patent [19]

Ackermann et al.

[11] 4,417,073
[45] Nov. 22, 1983

[54] PROCESS FOR THE PREPARATION OF SUBSTITUTED ACETIC ACIDS AND DERIVATIVES THEREOF

[75] Inventors: Otto Ackermann, Troisdorf; Gerhard Daum, Cologne, both of Fed. Rep. of Germany

[73] Assignee: Dynamit Nobel A.G., Troisdorf, Fed. Rep. of Germany

[21] Appl. No.: 324,929

[22] Filed: Nov. 25, 1981

[30] Foreign Application Priority Data

Nov. 29, 1980 [DE] Fed. Rep. of Germany ....... 3045102

[51] Int. Cl.³ ............................................. C07C 69/76
[52] U.S. Cl. .................................. 560/105; 560/265; 562/496; 562/606; 260/465 R; 260/465.1
[58] Field of Search ................. 562/606, 496; 560/265, 560/105; 260/465 R, 465.1

[56] References Cited

U.S. PATENT DOCUMENTS

| | | | |
|---|---|---|---|
| 1,939,212 | 12/1933 | Jaeger .................................. | 562/606 |
| 1,955,050 | 4/1934 | Brode et al. ........................ | 562/606 |
| 1,956,718 | 5/1934 | Jaeger .................................. | 562/606 |
| 1,961,150 | 6/1934 | Jaeger .................................. | 562/606 |
| 1,964,516 | 6/1934 | Jaeger .................................. | 562/606 |
| 1,966,067 | 7/1934 | Jaeger .................................. | 562/606 |
| 1,982,195 | 11/1934 | Brode et al. ........................ | 562/598 |
| 1,982,196 | 11/1934 | Brode et al. ........................ | 562/598 |
| 1,982,197 | 11/1934 | Brode et al. ........................ | 562/598 |
| 2,063,365 | 12/1936 | Conover ............................. | 562/606 |

FOREIGN PATENT DOCUMENTS

| | | | |
|---|---|---|---|
| 2854195 | 6/1980 | Fed. Rep. of Germany ...... | 562/606 |
| 2853732 | 7/1980 | Fed. Rep. of Germany ...... | 562/606 |
| 3130619 | 11/1980 | Japan .................................. | 562/598 |

*Primary Examiner*—Paul J. Killos
*Attorney, Agent, or Firm*—Felfe & Lynch

[57] ABSTRACT

A process for the preparation of substituted acetic acids and derivatives thereof, having the formula

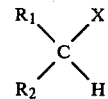 (I)

wherein
X is —COOH, —COOY or —CN,
Y is —CH$_3$ or —C$_2$H$_5$,
R$_1$ is a saturated, branched or unbranched aliphatic radical having from 1 to 6 carbon atoms, a phenyl radical, or a phenyl radical substituted by alkyl or alkoxy groups, and
R$_2$ is hydrogen or a saturated, branched or unbranched aliphatic radical having from 1 to 6 carbon atoms, a phenyl radical, or a phenyl radical substituted by alkyl or alkoxy groups,
wherein R$_1$ and R$_2$ may be the same or different which process comprises converting the corresponding malonic or cyanoacetic ester of the formula

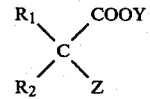 (II)

wherein
Z is —COOY or —CN, and
Y, R$_1$ and R$_2$ are identified as above at elevated temperature in the presence of a catalyst, e.g., a catalyst containing from about 50 to 75 weight percent SiO$_2$ and from 15 to 19 weight percent Al$_2$O$_3$ and exhibit ignition losses ranging from 15 to 20 weight percent.

15 Claims, No Drawings

PROCESS FOR THE PREPARATION OF SUBSTITUTED ACETIC ACIDS AND DERIVATIVES THEREOF

The invention relates to a process for the preparation of substituted acetic acids and their derivatives. Specifically the invention relates to a process for the preparation of substituted acetic acids, alkali-metal or alkaline-earth salts thereof, esters thereof and substituted acetonitriles thereof.

Among the great many compounds obtainable by the process in accordance with the invention are the homologs of acetic acids, for example, propionic acid, butyric acid, valeric acid, etc., and their nitriles. However, these acetic acids monosubstituted by unbranched aliphatic radicals usually are less preferred than branched-chain compounds and aryl-substituted acetic acids or acetonitriles.

Highly preferred is the preparation in accordance with the invention of bisubstituted acetic acids or acetonitriles.

Examples of such compounds are 2-phenylpropionic acid from phenylmethylmalonic acid esters, 2-phenylbutyric acid from phenylethylmalonic acid esters, 2-phenylvaleric acid from phenylpropylmalonic acid esters and phenylcycloalkylacetic acids from phenylcycloalkylmalonic esters as well as acetic acids substituted by two aliphatic radicals, such as 2-methylpropionic acid, 2-methylbutyric acid, 2-methylvaleric acid, 2-methylcaproic acid and dipropylacetic acid, which is also known as 2-propylvaleric acid. Dipropylacetic acid in the form of its salts is a well-known pharmaceutical product and as acid and/or ester therefore is a highly preferred end product of the process of the invention.

DISCUSSION OF THE PRIOR ART

The preparation of a number of substituted acetic acid esters from correspondingly substituted malonic acid esters through pyrolysis in the presence of catalysts is known.

For example, according to W. J. Bailey and J. J. Daly, J Org. Chem. 29 (5), 1964, 1249–51, phenylacetic acid is obtained through pyrolysis of phenolmalonic ester, and 3-methylcaproic acid through pyrolysis of methylbutylmalonic ester. Notwithstanding the high temperatures ranging from 457° to 560° C., only part of the substance is reacted and only a portion of that part is converted to the desired product.

Subsequently, it has therefore been proposed to prepare dipropylacetic acid by multiple-step reactions from butyric acid (German patent application DOS No. 28 44 638) or from n-valeraldehyde diallylacetal (German patent application DOS No. 28 44 636). However, these routes are complicated, and the yields of these processes, too, are not very high.

According to German patent application DOS No. 28 53 732, dipropylmalonic ester is formed from malonic acid diethyl ester. Then the pure dipropylmalonic acid is isolated by acidification, purified and dried. Only then is it decarboxylated at temperatures between 160° and 165° C., in other words, above the melting point, to dipropylacetic acid, which then must be purified by fractional distillation. Isolation of the pure dipropylmalonic acid constitutes an extra process step entailing high losses, with the result that a yield of only 42.9% is obtained, based on the starting product, malonic acid diethyl ester.

In these processes involving the saponification and decarboxylation of dipropylmalonic ester, there are formed per mole of malonic ester two moles of salt, which must be separated and disposed of. The conversion to dipropylacetic acid requires a considerable expenditure of equipment, substance and time since the malonic ester undergoes alkaline saponification and the alkali-metal salt must be converted to the acid by acidification in a separate apparatus.

When dipropylcyanoacetic ester is the starting material, saponification and decarboxylation of the ester group must be followed by hydrolysis of the nitrile group as an additional step. (German patent application DOS No. 27 21 264.)

SUMMARY OF THE INVENTION

It has now been found that it is possible to convert singly and doubly substituted malonic esters without prior formation of malonic acids, or singly or doubly substituted cyanoacetic acid esters, by simple means and in high yield to correspondingly substituted acetic acid esters or acetonitriles by the use of catalysts.

The invention thus has as its object a process for the preparation of substituted acetic acids and/or their esters or substituted acetonitriles of the formula (I)

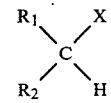

wherein X stands for —COOH, —COOY or —CN, Y for —CH$_3$ or —C$_2$H$_5$, R$_1$ for a saturated, branched or unbranched aliphatic radical having from 1 to 6 carbon atoms, a phenyl radical, or a phenyl radical substituted by alkyl or alkoxy groups, and R$_2$ for hydrogen or R$_1$, R$_1$ and R$_2$ being alike or different, from correspondingly substituted malonic or cyanoacetic esters of the formula (II)

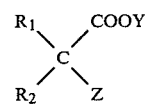

wherein Z stands for —COOY or —CN, and Y, R$_1$ and R$_2$ have the meanings given above, said process being characterized in that the malonic or cyanoacetic esters are converted at elevated temperature in the presence of catalysts.

Considerable advantages of the process are that it uses readily obtainable substituted malonic esters or substituted cyanoacetic esters; that these are converted nearly completely; that there is practically no formation of byproducts and products of decomposition; that relatively low reaction temperatures are employed; that, in contrast to the prior art, no salts formed by neutralization are to be disposed of; and that the overall costs of the process thus are substantially reduced.

It is highly preferred that the reaction be carried out in the presence of water, which will considerably facilitate complete conversion. The presence of water increases the proportion of the substituted acetic acid, which varies with the product and the reaction conditions, in relation to the substituted acetic acid ester. This is advantageous, particularly in view of the highly important further processing of the reaction products to salts of the substituted acetic acids.

Suitable amounts of water range from 1 to 50 moles, and preferably from 10 to 30 moles, of water per mole of the starting materials.

However, the reaction may also be carried out in the absence of water. Substituted acetic acid esters will then be formed as the chief product, along with substituted acetic acids.

The reaction may also be carried out in the presence of an alcohol, and especially of the alcohol corresponding to the ester group of the substituted malonic ester. In that case too, the product will be predominantly substituted acetic acid esters, along with small amounts of substituted acetic acid. Suitable amounts of alcohol also range from 1 to 50 moles per mole of starting material.

The reaction may also be carried out in the presence of both water and the corresponding alcohol.

The starting materials are readily available, for example, from malonic ester, which is manufactured industrially on a large scale, by reaction with alkyl halides, or from cyanoacetic ester, with reacts similarly.

The reaction temperature may range from 150° to 360° C. and preferably ranges from 180° to 300° C. It will be advantageous to employ as low a temperature as possible since there will then be little formation of by-products and decomposition of substance. The temperature to be employed depends on the activity of the catalyst used. The highly active catalysts listed further on will bring about some conversion even at 150° C. and exhibit optimum activity, with very high conversions and extremely small amounts of byproducts, at temperatures between 210° and 240° C., and more particularly between 220° and 230° C. Less active catalysts require temperatures of 300° C. and up.

The reactor may be a tubular reactor comprising an evaporation zone and a catalyst zone and advantageously is an upright, heated tube provided with the catalyst. The reactants are metered into the preheating zone at the top, with the water then evaporating. The malonic or cyanoacetic ester need not be present entirely in the vapor phase, which is a further positive factor since it permits the reaction to be carried out at relatively low temperatures. After the reaction mixture has passed through the catalyst zone, it is cooled and in the process separates into an aqueous phase and an organic phase, which then must be worked up separately. The liberated alcohol is largely present in the aqueous phase.

The alcohol may be recovered through distillation. The water, or mixture of water and alcohol, as the case may be, can be recycled to the reactor.

The desired substituted acetonitrile or substituted acetic acid and the corresponding ester are contained in the organic phase in a ratio that varies with the reaction conditions. The substituted acetic acid ester can readily be separated from the substituted acetic acid by fractional distillation since the boiling points are far apart.

Any residues of the starting compounds contained in the product will be present in the organic phase. In the case of dipropylacetic acid, for example, the starting material will distil over with the dipropylacetic acid and thus can be separated from the dipropylacetic acid ester. If necessary, the products or the fractions may be reacted once more along with further starting materials, which will not be detrimental. However, the great advance which the present catalytic pyrolysis process represents lies precisely in the fact that the presence of starting-material residues in the end product can be prevented almost completely by adhering to the temperatures and amounts of water specified and by using the catalysts listed below in layers of a depth appropriate to the requisite residence time.

Working up is preferably done by converting the entire organic phase to alkali-metal or alkaline-earth salts, and in particular to sodium and potassium or, optionally, calcium salts, without isolation of acid and ester, by treatment with the hydroxides in aqueous solution, with the salt forming immediately from the acid and the ester being saponified to the salt while the alcohol is split off.

Suitable catalysts are those of a siliceous and oxidic nature with a high $SiO_2$ and/or $Al_2O_3$ content but containing no heavy metals except for a little iron oxide. These catalysts generally exhibit a loss on ignition due to their moisture content.

The activity of these catlaysts varies widely as a function of the properties set forth below.

Highly active and highly preferred are catalysts which contain both $SiO_2$ and $Al_2O_3$ (group I), exhibit an ignition loss, and may further contain small amounts of CaO, MgO and $K_2O$ in addition to small amounts of $Na_2O$. The most active group of catalysts contains from about 50 to 75 weight percent $SiO_2$ and about 15 to 19 weight percent $Al_2O_3$, with an ignition loss ranging from 15 to 20 weight percent, along with from 2.5 to 5.5 weight percent CaO, MgO and $K_2O$ combined, in addition to low contents of $Na_2O$ ranging from 0.1 to 0.4 weight percent and of $Fe_2O_3$ ranging from 2.5 to 4.0 weight percent.

These highly active catalysts may be produced from montmorillonite or other appropriate natural silicates through an acid treatment, drying, and preparation for use as catalysts.

With this group of catalysts, conversions of the starting materials of better than 99.9% can be obtained at the optimum temperature, which ranges from 210° to 240° C., and more particularly from 220° to 230° C. However, the activity of the catalysts is not limited to this temperature range.

So far as can be determined, the high activity of these catalysts is due to the natural moisture content and structure of the silicate, which are preserved, in whole or in part, during the acid and preparatory treatments, as well as to their specified $SiO_2$ and $Al_2O_3$ contents, while the MgO, CaO and $K_2O$ contents, the low $Na_2O$ content and also the iron oxide content, which are due to origin and preparation, are not regarded as essential to their catalytic activity.

Another group of catalysts, group II, is less active and less preferred. These catalysts may also contain MgO, CaO, $K_2O$, $Na_2O$ and iron oxides and may be prepared as indicated above but contain (a) from 85 to 92 weight percent $SiO_2$ and up to 2 weight percent $Al_2O_3$, with ignition losses ranging from 6.5 to 8.5 weight percent, or (b) from about 68 to 75 weight percent $SiO_2$ and from 14 to 16 weight percent $Al_2O_3$, with an ignition loss ranging from 6.5 to 8.5 weight percent.

The reaction temperatures of this group of catalysts are optimum from 250° C. on, and more particularly over the range from 260° to 290° C. However, the conversions obtained will not always be over 99.9% but often just over about 98.5%, and the yields based on the conversion will not be consistently above about 92 to 94%.

Suitable for use are also the catalysts of group III, which consist practically in their entirety of Al₂O₃ and are marketed as catalyst carriers. Their reduced activity, especially in relation to that of the highly preferred group, manifests itself in that at temperatures between 250° nd 260° C. conversion, at from 55 to 60, is incomplete although the yield is in excess of 97% of conversion, whereas at from 240° to 260° C. conversion is high, over 98%, though the yield is diminished due to decomposition.

The particle size of the materials used as catalysts usually ranges from 1.5 to 8 mm.

The service life of the catalysts is good, and they need to be regenerated only at relatively large intervals of time. In continuous operation, it is advisable to compensate for the gradually declining catalyst activity by slightly increasing the reaction temperature. However, the latter should not be raised to the point where an appreciable increase in decomposition sets in.

Regeneration is indicated only when the catalyst activity has dropped considerably. In practice, it is readily carried out by the procedure set forth below.

An amount of water equal to or as much as double the weight of the catalyst is conducted through the reactor at 300° C. Then air is introduced, also at about 300° C., for about 2 to 3 hours. This treatment will restore the catalyst to full activity.

In the tests run, there was no need to replace the catalyst because of loss of activity even after repeated regeneration.

The catalysts listed below were used. The contents are in weight percent.

| Catalyst | Ignition loss | SiO$_2$ | Al$_2$O$_3$ | CaO | MgO | Fe$_2$O$_3$ | Na$_2$O | K$_2$O | Total |
|---|---|---|---|---|---|---|---|---|---|
| Ia | 18.7 | 58.5 | 15.2 | 0.26 | 1.01 | 2.80 | 0.33 | 1.43 | 98.2 |
| Ib | 13.3 | 55.1 | 18.7 | 1.68 | 2.05 | 3.87 | 0.29 | 1.52 | 96.5 |
| Ic | 16.7 | 55.9 | 18.1 | 1.75 | 2.00 | 3.70 | 0.27 | 1.49 | 99.9 |
| Id | 14.9 | 62.2 | 16.2 | 0.24 | 1.29 | 2.85 | 0.19 | 1.22 | 99.1 |
| Ie | 15.4 | 63.4 | 15.8 | 0.16 | 1.28 | 2.74 | 0.13 | 1.01 | 99.9 |
| IIa | 8.2 | 71.3 | 15.6 | 0.17 | 1.13 | 2.65 | 0.13 | 1.12 | 100.3 |
| IIb | 7.2 | 90.4 | 1.3 | 0.13 | 0.10 | 0.23 | 0.0084 | 0.12 | 99.5 |

Apparatus

The reactor used was an upright, electrically heated quartz tube with an inside diameter of 30 mm which was filled with the catalyst and onto which an evaporator tube of the same diameter and filled with porcelain saddles had been set. The latter tube was also electrically heated, through a separate circuit, and was provided with feed lines for the starting substance and for water or alcohol. At the lower end of the reactor, a two-neck flask was disposed which had a reflux condenser set onto it in which the product collected. The reactants were metered by means of diaphragm pumps, and the waste gases were conducted from the reflux condenser through a cold trap to an exhaust. The temperature was measured by means of thermocouples disposed concentrically in the reactor and in the evaporator tube inside a thin protective quartz tube.

EXAMPLE 1

1600 g, or 6.552 moles, dipropylmalonic acid diethyl ester and 2192 g, or 121.8 moles, water were metered over a period of 19.3 hours through the evaporator tube into the reactor, filled with 450 kg of catalyst IIb of the foregoing table in bead form (diameter, about 6 mm).

The reaction temperature ranged from 298° to 312° C.

In the flask, the reaction mixture separated into an aqueous bottom layer and an organic top layer. The separated organic phase of 1051 g was fractionally distilled under a vacuum of 22 millibars by the use of a 40-cm tall packed column with porcelain saddles.

The yield was:
484 g, or 2.808 moles, dipropyl acetic acid ethyl ester (boiling point at 22 millibars, 77° to 78° C.), representing a yield of 43.7%, based on the reacted dipropylmalonic ester, and
409 g, or 2.836 moles, dipropylacetic acid (boiling point at 22 millibars, 122° to 123° C.), representing a yield of 44.3%, based on the reacted dipropylmalonic ester, while
32 g, or 0.131 mole, dipropylmalonic ester distilled over along with the dipropylacetic acid.

The conversion of dipropylmalonic ester was 98% of theory. Dipropylacetic acid and dipropylacetic acid ethyl ester combined reepresented an effective total yield of 87.9%.

Catalyst IIa gives similar results when like amounts are used.

EXAMPLES 2 to 4

Abbreviations:
DPMDE = Dipropylmalonic acid diethyl ester
DPMDM = Dipropylmalonic acid dimethyl ester
DPA = Dipropylacetic acid
DPAE = Dipropylacetic acid ethyl ester
DPAM = Dipropylacetic acid methyl ester By the procedure of Example 1 and employing the apparatus outlined, but using the highly active catalysts Ic and Id, respectively, of the foregoing table, the following ressults were obtained under the conditions set forth below, with practically complete conversion of the starting materials:

| Feed | Example 2 DPMDE | Example 3 DPMDE | Example 4 DPMDM |
|---|---|---|---|
| Amount, g/moles | 4100/16.79 | 913/3.74 | 500/2.31 |
| Water, g/moles | 7556/419.8 | 1513/84.06 | 887/49.28 |
| Amount of catalyst, g | Ic: 450 | Ie: 450 | Ie: 450 |
| Particle size, mm | Granules, 1.5–5 mm | Granules, 1.5–5 mm | Granules, 1.5–5 mm |
| Temperature, °C. | 220–223 | 220–222 | 229–230 |
| Duration (metering-in time), hours | 55.4 | 11.28 | 6.37 |
| Conversion, percent | ≧99.9 | ≧99.9 | ≧99.9 |

Similar results as in Example 2 were obtained when like amounts of catalysts Ia, Ib and Ic were used.

|  | Example 2 DPMDE | Example 3 DPMDE | Example 4 DPMDM |
|---|---|---|---|
| Yield, in percent, based on conversion, of: | | | |
| DPA | 42.5 | 44.1 | 33.0 |
| DPAE | 53.9 | 48.0 | |
| DPAM | | | 61.3 |
| DPA + DPAE | 96.4 | 92.1 | |
| DPA + DPAM | | | 94.3 |

EXAMPLE 5

Preparation of the sodium salt from the mixture of dipropylacetic acid and dipropylacetic acid ester 400 g of the organic phase of the reaction product was withdrawn from a continuous test involving the conversion of dipropylmalonic acid diethyl ester to dipropylacetic acid and dipropylacetic acid ethyl ester. Analysis by gas chromatography showed that it contained less than 0.1 weight percent of the starting substance and less than 0.2 weight percent valeric acid. Through boiling with NaOH and back titration, acid and ester were determined to total 2.381 moles. This reaction solution was mixed with 324 g of an aqueous 29.4 wt. % NaOH solution (2.381 moles NaOH) and refluxed for 3 hours. The residual alkali content was found to be 0.08%, or 0.58 g NaOH.

Neutralization was carried out by the addition of 2 g dipropylacetic acid. Ethanol was distilled off and water was then discharged azeotropically with 450 ml toluene.

The content of the flask was then evaporated on a rotary evaporator, first in a water-jet vacuum and then in an oil-pump vacuum, to dryness. After drying at 80° C. and 20 millibars over $CaCl_2$, 388 g sodium dipropyl acetate representing a 97.7% yield was obtained.

The dipropylacetic acid liberated after acidification with concentrated HCl had a purity of 99.47%.

The remaining 0.53% was made up of dipropylmalonic acid (0.016), valeric acid (0.28), dipropylacetic ester (0.047) and three unknown compounds.

EXAMPLES 6 to 14

By the procedure of Example 1 and employing the apparatus described, monosubstituted malonic acid esters were converted in Examples 6 to 9 (Table 1), and disubstituted malonic esters and a disubstituted cyanoacetic acid ester, in Examples 10 to 12 (Table 2). In Example 13, alcohol was used in place of water. Example 14 was carried out in the absence of water and alcohol, and in Example 15 (Table 3) an $Al_2O_3$ catalyst was used.

It will be appreciated that the instant specification and examples are set forth by way of illustration and not of limitation, and that various changes and modifications may be made without departing from the spirit and scope of the present invention.

TABLE 1

| Feed | Example 6 Ethylmalonic ester | Example 7 Propylmalonic ester | Example 8 Butylmalonic ester | Example 9 Phenylmalonic ester |
|---|---|---|---|---|
| Amount in grams/moles | 180/0.956 | 374/2.147 | 200/0.925 | 561/2.37 |
| Water, grams/moles | 230/12.76 | 837/46.5 | 200/11.11 | 831/46.2 |
| Catalyst, grams | IIb/450 | Ie/450 | IIb/450 | Ic/500 |
| Particle size, mm | Beads/6 | Granules/1.5–5 | Beads/6 | Granules/1.5–5 |
| Temperature, °C. | 285–288 | 200–201 | 288 | 259–260 |
| Reaction time, hours | 1.84 | 6.23 | 1.92 | 6.25 |
| Conversion, percent | ≧99.9 | ≧99.9 | ≧99.0 | ≧99.9 |
| Yield based on conversion in percent of theory of: | | | | |
| Butyric acid | 21.4 ⎫ 80.6 | | | |
| Butyric acid ethyl ester | 59.2 ⎭ | | | |
| Valeric acid | | 24.4 ⎫ 92.6 | | |
| Valeric acid methyl ester | | 68.2 ⎭ | | |
| Caproic acid | | | 39.6 ⎫ 98.6 | |
| Caproic acid ethyl ester | | | 59.0 ⎭ | |
| Phenylacetic acid | | | | 45.8 ⎫ 89.5 |
| Phenylacetic acid ethyl ester | | | | 43.7 ⎭ |

TABLE 2

| Feed | Example 10 Diethylmalonic ester | Example 11 Phenylethyl-malonic ester | Example 12 Dipropylcyano-acetic acid |
|---|---|---|---|
| Amount in grams/moles | 180/0.832 | 60/0.227 | 374/1.896 |
| Water, grams/moles | 271/15.1 | 90/5.0 | 481/26.71 |
| Catalyst, grams | IIb/450 | IIb/450 | IIb/450 |
| Particle size, mm | Beads/6 | Beads/6 | Beads/6 |
| Temperature, °C. | 285 | 260–270 | 290 |
| Reaction time, hours | 1.94 | 1 | 4.49 |
| Conversion, percent | 91.7 | 97.4 | 82.2 |
| Yield based on conversion in percent of theory of: | | | |
| Diethylacetic acid | 33.0 ⎫ 96.3 | | |
| Diethylacetic acid ethyl ester | 63.3 ⎭ | | |
| Phenylethylacetic acid | | 41.6 ⎫ 77.7 | |

TABLE 2-continued

| Feed | Example 10 Diethylmalonic ester | Example 11 Phenylethyl- malonic ester | Example 12 Dipropylcyano- acetic acid |
|---|---|---|---|
| Phenylethylacetic acid ethyl ester | | 36.1 | |
| Dipropyl acetonitrile | | | 82.0 |

TABLE 3

| | | | Example 15 | |
|---|---|---|---|---|
| Feed | Example 13 Dipropylmalonic ester | Example 14 Dipropylmalonic ester | (a) Dipropylmalonic ester | (b) Dipropylmalonic ester |
| Amount in grams/moles | 81.4/0.333 | 122.2/0.50 | 80/0.327 | |
| Ethanol or water, grams/moles | 138.0/3.0[1] | — | 131/7.28[2] | 127/7.06[2] |
| Catalyst, grams | Ic/500 | Ic/500 | Al$_2$O$_3$ 250/200 | |
| Particle size, mm | Granules/1.5–5 | Granules 1.5–5 | Beads/6 | |
| Temperature, °C. | 219–220 | 239–240 | 251–253 | 351–352 |
| Reaction time, hours | 1.07 | 1.1 | 1 | 0.98 |
| Conversion, percent | ≅99.9 | 90.6 | 59.0 | 98.1 |
| Yield based on conversion in percent of theory of: | | | | |
| Dipropylacetic acid | 7.8 ⎫ 94.0 | 2.0 ⎫ 98.7 | 8.0 ⎫ 97.2 | 49.7 ⎫ 87.5 |
| Dipropylacetic acid ethyl ester | 86.2 ⎭ | 96.7 ⎭ | 89.2 ⎭ | 37.8 ⎭ |

[1]Ethanol
[2]Water

It will be understood that the specification and examples are illustrative but not limitative of the present invention and that other embodiments within the spirit and scope of the invention will suggest themselves to those skilled in the art.

What is claimed is:

1. A process for the preparation of substituted acetic acids and derivatives thereof, having the formula

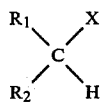

(I)

wherein
X is —COOH, —COOY or —CN,
Y is —CH$_3$ or —C$_2$H$_5$,
R$_1$ is a saturated, branched or unbranched aliphatic radical having from 1 to 6 carbon atoms, a phenyl radical, or a phenyl radical substituted by alkyl or alkoxy groups, and
R$_2$ is hydrogen or a saturated, branched or unbranched aliphatic radical having from 1 to 6 carbon atoms, a phenyl radical, or a phenyl radical substituted by alkyl or alkoxy groups,
wherein R$_1$ and R$_2$ may be the same or different which process comprises converting the corresponding malonic or cyanoacetic ester of the formula

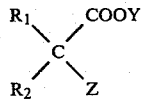

(II)

wherein
Z is —COOY or —CN, and
Y, R$_1$ and R$_2$ are identified as above, at a temperature ranging from 150° C. to 360° C. in the presence of a catalyst essentially free of heavy metals except for small amounts of iron oxide impurities and comprising substances of an oxidic or siliceous nature containing at least one of the elements Si and Al.

2. Process as claimed in claim 1, wherein the conversion is carried out in the presence of water.

3. A process as claimed in claim 2, wherein the amount of water used ranges from 1 to 50 moles per mole of malonic or cyanoacetic ester.

4. A process as claimed in claim 1, wherein the conversion is carried out in the presence of the alcohol corresponding to the ester group of the malonic or cyanoacetic ester.

5. A process as claimed in claim 4, wherein the alcohol is used in amounts ranging from 1 to 50 moles per mole of malonic or cyanoacetic ester.

6. A process as claimed in claim 1, wherein the conversion is carried out in the absence of water or alcohol.

7. A process as claimed in claim 1, wherein the conversion is preferably carried out at temperatures ranging from 180° to 300° C.

8. A process as claimed in claim 1, wherein the catalyst substances may optionally contain the elements Fe, Mg, Ca, K and Na as further constituents.

9. A process as claimed in claim 1, wherein the catalyst contains from about 50 to 75 weight percent SiO$_2$ and from 15 to 19 weight percent Al$_2$O$_3$ and exhibit ignition losses ranging from 15 to 20 weight percent.

10. A process as claimed in claim 1, wherein the catalyst contains from about 85 to 92 weight percent SiO$_2$ and up to 2 weight percent Al$_2$O$_3$ and exhibit ignition losses ranging from 6.5 to 8 weight percent.

11. A process as claimed in claim 1, wherein the catalyst contains from about 68 to 75 weight percent SiO$_2$ and from 14 to 16 weight percent Al$_2$O$_3$ and exhibit ignition losses ranging from 6.5 to 8 weight percent.

12. A process as claimed in claim 1, wherein the catalyst consists essentially of Al$_2$O$_3$.

13. A process as claimed in claim 1, wherein the products are obtained by separating the aqueous and organic phases formed and by working up the organic phase to give the products.

14. A process as claimed in 13, wherein the organic phase is separated by distillation into the particular substituted acetic acid and the corresponding substituted acetic acid ester.

15. A process as claimed in claim 13, wherein the entire organic phase containing substituted acetic acid and the corresponding ester is converted to the alkali-metal or alkaline-earth salts of the acid by heating with the appropriate hydroxides.

* * * * *